(12) United States Patent
Tate et al.

(10) Patent No.: US 6,904,820 B2
(45) Date of Patent: Jun. 14, 2005

(54) METHOD OF USING A SIMULATED SKIN SUBSTRATE AND METHOD FOR DETERMINING MATERIAL DRYNESS PERFORMANCE

(75) Inventors: Martha L. Tate, Atlanta, GA (US); Audra S. Wright, Woodstock, GA (US); Nancy H. Puckett, Roswell, GA (US); Andrea S. Wulz, Roswell, GA (US); Susan C. Paul, Alpharetta, GA (US); Jason Cohen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/324,605

(22) Filed: Dec. 20, 2002

(65) Prior Publication Data

US 2004/0118224 A1 Jun. 24, 2004

(51) Int. Cl.⁷ .............................................. G01N 33/00
(52) U.S. Cl. ....................................................... 73/866
(58) Field of Search ............................. 73/25.04, 29.01, 73/29.02, 73, 866, 866.4

(56) References Cited

U.S. PATENT DOCUMENTS

| | | |
|---|---|---|
| 1,561,285 A | 11/1925 | Sesler |
| 2,545,281 A | 3/1951 | Hunt |
| 3,341,394 A | 9/1967 | Kinney |
| 3,502,538 A | 3/1970 | Peterson |
| 3,502,763 A | 3/1970 | Hartmann |
| 3,542,615 A | 11/1970 | Dobo et al. |
| 3,952,584 A | 4/1976 | Lichstein |
| 4,041,203 A | 8/1977 | Brock |
| 4,257,188 A | 3/1981 | Barker |
| 4,340,563 A | 7/1982 | Appel et al. |
| 4,357,827 A | 11/1982 | McConnell |
| 4,720,415 A | 1/1988 | Vander Wielen et al. |
| 4,932,919 A | 6/1990 | Shapero |
| 5,066,259 A | 11/1991 | Acker |
| 5,067,924 A | 11/1991 | Munter |
| 5,361,627 A | 11/1994 | Levesque |
| 5,419,729 A | 5/1995 | Gross |
| 5,425,265 A | 6/1995 | Jaisinghani |
| 5,518,436 A | 5/1996 | Lund et al. |
| 5,913,708 A | 6/1999 | Gross |
| 5,979,235 A * | 11/1999 | Kurz et al. ................ 73/432.1 |
| 6,015,935 A | 1/2000 | LaVon et al. |
| 6,085,579 A * | 7/2000 | Herrlein ........................ 73/73 |
| 6,107,537 A | 8/2000 | Elder et al. |
| 6,152,906 A | 11/2000 | Faulks et al. |
| 6,298,714 B1 * | 10/2001 | Courtray ....................... 73/73 |
| 6,413,142 B1 | 7/2002 | Weastler |
| 6,446,495 B1 * | 9/2002 | Herrlein et al. ............... 73/73 |
| 6,464,557 B1 | 10/2002 | Ohba et al. |
| 6,503,525 B1 | 1/2003 | Paul et al. |
| 6,534,074 B2 | 3/2003 | Krzysik et al. |
| 6,557,398 B2 | 5/2003 | Lindmark et al. |
| 2002/0191669 A1 * | 12/2002 | Fan et al. .................... 374/45 |

FOREIGN PATENT DOCUMENTS

GB  2272182 A  5/1994

OTHER PUBLICATIONS

U.S. Appl. No. 10/324,884, filed Dec. 20, 2002.
U.S. Appl. No. 10/324,834, filed Dec. 20, 2002.
U.S. Appl. No. 10/324,365, filed Dec. 20, 2002.

* cited by examiner

*Primary Examiner*—Charles Garber
(74) *Attorney, Agent, or Firm*—Dority & Manning, P.A.

(57) ABSTRACT

Methods of using an evaluation apparatus for pre-screening a material for use in an absorbent article are provided. The evaluation apparatus includes a simulated body part having a simulated skin substrate. The material is placed proximate the simulated skin substrate, and a predetermined amount of simulated physiological fluid is insulted into the material at a pre-measured location. After a predetermined time, the simulated skin substrate is removed from the body part and fluid loss measurements are taken.

28 Claims, 3 Drawing Sheets

METHOD OF USING A SIMULATED SKIN SUBSTRATE AND METHOD FOR DETERMINING MATERIAL DRYNESS PERFORMANCE

BACKGROUND OF THE INVENTION

Absorbent articles such as diapers, adult incontinence garments, feminine care products, child training pants, pull-ups, bandages, gloves and similar products that directly contact skin are well known. A disposable absorbent article is typically composed of a top layer that is adjacent to a user's body and a back layer that faces the clothing of the user. An absorbent material is located between the top layer and the bottom layer. The top layer permits a liquid from the user to move through the top layer toward the back layer. The back layer does not allow liquid to be transferred from the inside of the absorbent article onto the user's clothing. The absorbent material absorbs the liquid and keeps the skin dry.

During normal operation after a fluid is discharged from a user, the fluid will flow through the top layer and be absorbed by the absorbent material. The absorbent material is designed to absorb, redistribute, and store the fluid until the absorbent article is discarded. In some instances, however, fluid may return from the absorbent material to once again contact the user's skin. Fluid return would occur, for example, if the absorbent material was insufficiently composed to absorb the fluid. Unabsorbed fluid undesirably results in over-hydration of the contacted skin and in turn, increases a chance of skin irritation to the user. In addition to being an irritant, excessive moisture on the user's skin can cause, among other things, the growth of microorganisms that can lead to the onset of rashes or infection.

Various tests exist for measuring performance and suitability of absorbent materials to prevent the foregoing problems. Known tests include capacitance, conductance, electrical impedance, gravimetric, and/or evaporative or Trans-Epidermal Water Loss (TEWL) evaluations. Typically, these tests measure fluid absorbency, fluid leakage, and other criteria of the materials for use in absorbent articles.

One such test is the Adult Forearm Test or "armband" test, which is conventionally used to evaluate the effectiveness of disposable diapers to keep the skin dry. A variation of the armband test uses pre-loaded patches from diapers placed on an adult volar forearm. Changes in skin surface hydration are measured by evaporimetry or TEWL evaluation. Differences in skin surface hydration between cloth diapers and disposable paper diapers have been noted using this armband test variant.

Another armband test uses an intact diaper wrapped around the forearm. Physiological saline is injected into the diaper at a rate and volume that represent normal urination by a child. Post-occlusion measurements are made after one hour, and measurements of skin hydration are made by computerized evaporimetry or by electrical conductance.

BRIEF SUMMARY OF THE INVENTION

In general, the present invention utilizes a simulated skin substrate to evaluate materials quickly, efficiently and cost effectively. The simulated skin is attached to an evaluation apparatus as a pre-screening tool for evaluating materials for diaper, childcare, feminine care, adult care, health care, competitive and other products without initially using human subjects. The component parts of the invention are simple, reliable, and economical to manufacture and use. As used herein, the terms "simulated," "virtual," "artificial," "synthetic" and like terms are used interchangeably to indicate manufactured materials or objects, and in the case of substrates, dissected or bioengineered skin samples, unless otherwise indicated.

In one aspect of the invention, a silicone, neoprene or similar material forms a mechanical torso, such as an infant torso. As used herein, the terms "torso", "mannequin" and like terms are used interchangeably to indicate simulated body parts, unless indicated otherwise. The simulated infant torso incorporates a fluid injection port, which simulates a sweat gland, a pore, a urethra or similar orifice. A simulated skin substrate such as VITRO-SKIN™ is placed on a portion of the torso proximate the fluid injection port, for example, on the front of the torso in a suprapubic area. A material is wrapped about the simulated skin substrate and the fluid injection port. The material is insulted with saline or other simulated physiological fluid. After a predetermined time, the material is removed and the skin is evaluated for dryness. To measure water loss or wetness, the evaluation can be conducted, for instance, with a Trans-Epidermal Water Loss (TEWL) probe.

In another aspect of the invention, a mechanical arm includes a Plexiglas®-type cylinder arranged to simulate an adult forearm for rapidly pre-screening and ranking a material for further evaluation, possibly on human subjects. The arm incorporates a fluid injection port, which simulates a sweat gland, a pore, a urethra, a body cavity, etc. and the like. A simulated skin substrate is placed on a portion of the arm proximate the fluid injection port. The material is wrapped about the simulated skin substrate and the fluid injection port and insulted with saline or other simulated physiological fluid. After a predetermined time, the material is removed and the skin is evaluated for dryness in a manner similar to the previous embodiment.

In a further aspect of the invention, an exemplary method is provided for evaluating a material insulted with a fluid from a fluid delivery device. The method includes the steps of providing an object with a fluid injection port and a heater arrangement; at least partially covering the object with an artificial skin; at least partially covering the object, the heater arrangement, and the artificial skin with the material; insulting the fluid from the fluid delivery device into the material via the fluid injection port; and assessing the fluid-insulted material and a condition of the artificial skin.

Thus, the present invention enables rapid pre-screening of materials by using economical artificial components and avoiding variables in a population of human subjects. Other aspects and advantages of the invention will be apparent from the following description and the attached drawings, or can be learned through practice of the invention.

In a further aspect of the invention, a method is provided to measure differences between materials combination in product form for dryness. This method can be used to prescreen materials for TEWL.

BRIEF DESCRIPTION OF THE DRAWINGS

The above and other aspects and advantages of the present invention are apparent from the detailed description below and in combination with the drawings in which.

Repeat use of reference characters in the drawings and the detailed description is intended to represent same or analogous features or elements of the invention.

DETAILED DESCRIPTION OF THE DRAWINGS

Detailed reference will now be made to the drawings in which examples embodying the present invention are shown. The drawings and detailed description provide a full and detailed written description of the invention and the manner and process of making and using it, so as to enable one skilled in the pertinent art to make and use it. The drawings and detailed description also provide the best mode of carrying out the invention. However, the examples set forth herein are provided by way of explanation of the invention and are not meant as limitations of the invention. The present invention thus includes modifications and variations of the following examples as come within the scope of the appended claims and their equivalents.

In general, the present invention is directed to a method of using a simulated skin for use with an evaluation apparatus for quickly pre-screening or bench testing products or materials without the initial need for human subjects. Once the materials are pre-screened, a determination can be made as to which materials warrant additional testing and evaluation, possibly on human subjects. The materials, for example, may include an absorbent material, disposable or non-disposable diapers, diaper systems, adult incontinence products, feminine products, nursing healthcare products, child training products, bandages, gloves, face masks, and similar disposable and non-disposable products that contact a consumer's skin. Additionally, the material can be a nonwoven polymer material, an airlaid material, a wet material, a dry material, a treated material, and disposable or non-disposable materials.

Figure 1:
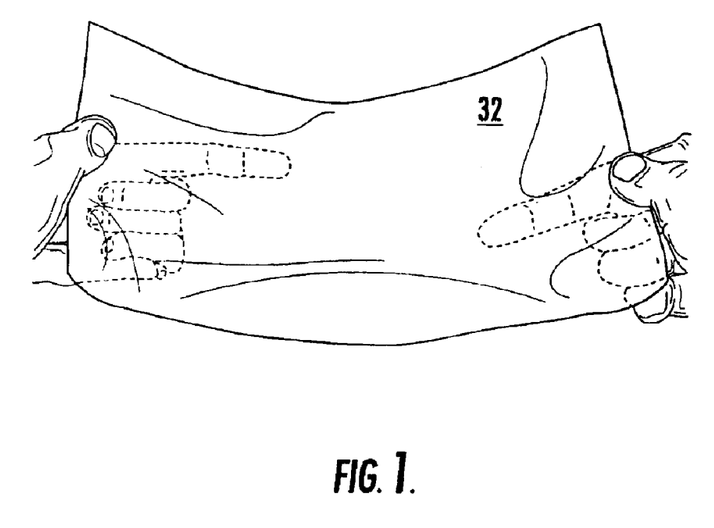
FIG. 1 is a perspective view of a portion of simulated skin in accordance with aspect of the invention.

Referring to FIG. 1, a portion of the simulated skin 32 is shown. By way of brief introduction, a material 36 is disposed about the skin 32 and insulted with a fluid 28. The fluid 28 may be water, saline, natural or simulated menses fluid, urine, breast milk, or blood, a solution of 0.9% sodium chloride, a colored solution, an exudate or any suitable material for simulating human body fluids. After a predetermined time, the material 36 is removed, and the simulated skin 32 is evaluated for wetness/dryness. A more detailed example of the operation of these components is described below.

A variety of simulated skin materials and products are suitable for use as simulated skin 32 to demonstrate the hydration and/or moisturization properties of personal care products, diapers and the like. Examples include but are not limited to VITRO-SKIN™ and VITRO-CORNEUM® available from IMS Inc., Milford, Conn.; TEST SKIN™ II from Organogenesis Inc., Canton, Mass.; SKINETHIC® from Skinethic Tissue Culture Laboratories, Nice, France; EpiDerm™ simulated human skin from MatTek Corporation, Ashland, Mass.; a medical grade collagen film; a collagen in a sausage casing; cellulose film, a custom prepared chamois available from Acme Sponge and Chamois Company, Tarpon Springs, Fla.; a cultured or bioengineered skin substrate; a living/preserved skin sample from animal models such as but not limited to a pig, a monkey and a human cadaver; and similar materials.

By way of example, VITRO-SKIN™ substrate contains protein and lipid components and is designed to have topography, pH, critical surface tension and ionic strength that mimic human skin. Its consistent topography ("N-19 topography") and wetting properties across each sheet of VITRO-SKIN™ are optimized to mimic relatively smooth skin found on the human back. Thus, testing done on VITRO-SKIN™ is generally more reproducible than that performed on variable human skin samples due to the consistent topography of VITRO-SKIN™. In comparison, VITRO-CORNEUM® is a collagen-based substrate with properties similar to human stratum corneum. VITRO-CORNEUM® substrate is designed to simulate the thickness, visco-elasticity and surface properties of human stratum corneum; i.e., the outer layer of epidermis of primarily dead skin cells. The EpiDerm™ bioengineered human skin incorporates stratified epidermal layers, including a functional stratum corneum.

Another suitable simulated skin substrate is collagen in a sausage casing, Collagen is a cost-effective alternative for pre-screening materials 36 since collagen does not have to be handled and stored as a biological sample. An exemplary collagen is available from NATURIN GmbH, Weinhein, Germany, under the designation of COFF12224. COFF12224 is a collagen film having a basis weight of about 28 g/m$^2$. Another exemplary collagen film is available from Devro, Inc, Geneva, Ill., under the designation of Cutisin™.

Figure 2:
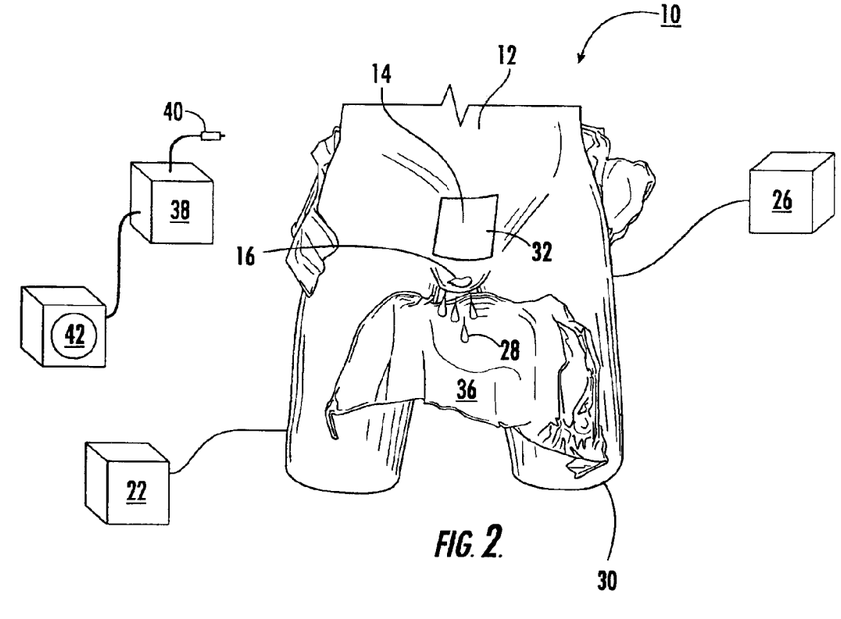
FIG. 2 is a perspective view of an evaluation apparatus in accordance with an aspect of the invention.

Referring to FIG. 2, there is shown a perspective view of one embodiment of the evaluation apparatus 10 utilizing a torso 12 with a fluid injection port 16 for insulting the fluid 28 into the material 36. The fluid 28 can be preloaded in the material 36 prior to placing the material 36 on the torso 12; or insulted via a syringe (not shown) after the material 36 is placed on the torso 12; or insulted via a fluid delivery device 26, using a tubing or fluid tube (not shown) disposed externally or within the torso 12. For example, to prevent external forces from disturbing the tube, it can be attached to the fluid delivery device 26 and routed within the torso 12 to deliver the fluid 28 through the fluid injection port 16. Alternatively, the tube can be arranged outside the torso 12. In this aspect, the tube is secured by tape or other fastening devices and positioned to emit the fluid 28 at a point similar to the fluid injection port 16. Examples of fluid loading are described in greater detail below.

The exemplary torso 12 is approximately the size of an infant and adjustably attached to a base 30 to facilitate the TEWL measurements that are described below. It is to be understood that the injection port 16 can be sized to accommodate various fluid loading protocols utilized to simulate various human age groups and bodily functions. For instance, the injection port 16 can be sized to simulate a tear duct, a urethra, a pore, a vaginal opening or other body cavity. This aspect of the invention will be described in greater detail in the Experiments sections below.

In the example shown in FIG. 2, the torso 12 is formed of a silicone rubber material. The torso 12 further includes an attachment area 14 to which the simulated skin 32 is attached in a conventional manner. Although the exemplary torso 12 is formed of rubber, other materials such as acetyl plastic, an acrylic plastic, elastomeric materials, high density polyethylene, polymers, metals, glass, composite materials or Plexiglas®-type are suitable. Also, while the illustrated torso 12 is representative of an infant, it is not intended as a limitation of the invention. It is to be understood that other simulated anatomical parts representing, for instance, those of a man, woman, child, infant, or animal may be substituted for torso 12. For example, torso 12 can be a lower-torso mannequin, an upper-torso mannequin, a full-body mannequin, a mannequin forearm, a mannequin hand, a mannequin leg, a mannequin foot, a mannequin head or other simulated body parts.

FIG. 2 further shows fluid delivery device 26. The fluid delivery device 26 may be a digital pump or a computer controlled pump, which delivers a predetermined amount of fluid through the torso 12. A Masterflex® Computerized Water Pump, available from Cole-Parmer of Vernon Hills, Ill., is a suitable fluid delivery device, although comparable pumps can be substituted. In this example, the Cole-Parmer Masterflex® Computerized Water Pump can be operated via a Windows® Linkable Instrument Network (WINLIN) software program to link multiple pumps and mixers and synchronized and unsynchronized sequences of operation. Other features of the WINLIN program include:

Control of up to 25 pumps and mixers

Flow calibration by volume, weight or flow reference

Multiple flow, volume and torque units

Dispenses volumetrically or gravimetrically

Constant or ramped flow/speed control

The foregoing features provide laboratory technicians, materials evaluators and similar professionals the capabilities to insult predetermined amounts of fluid at predetermined times. Further, the Cole-Parmer Water Pump can be programmed to insult fluids in rapid succession or at selected time intervals depending on particular biological functions to be simulated. For instance, an adult incontinence product insult may be 105 milliliters (ml) to at least 480 ml. The protocol for insulting 105 ml or 480 ml are as follows: 3 leadings of 35 ml, 45 seconds apart, at 6 ml/sec (105 ml total) and 3 loadings of 75 ml, 15 minutes apart at 8 ml/sec (total of 480 ml for a large size product).

FIG. 2 also shows the measuring device 38, briefly introduced above. The measuring device 38 has the stand mounted or hand-held probe 40 used to determine skin dryness, diaper pooling, skin saturation and the like. The probe 40 is used to take TEWL measurements from the skin 32 after insulting the material 36 with the fluid 28, also as briefly introduced above. By way of example, a DermaLab® Trans-Epidermal Water Loss (TEWL) probe, developed by Cortex Technology, Denmark, available from cyberDERM, Inc. Media, Pa. is a suitable measuring device 38, although any comparable probe may be used. An electronic display unit or monitor 42 can be electronically attached to the measuring device 38 to display the TEWL measurements. The measuring device 38 and/or the monitor 42 can include recording capabilities to automatically save the TEWL measurements to a magnetic tape, hard drive, disc or the like. It is to be noted that the measuring device 38 can be provided to measure capacitance, conductance, electrical impedance, and/or substrate weight instead of or in addition to TEWL. Further details of the testing protocol and operation of the apparatus 10 and its measuring device 38 are discussed below.

Figure 3:
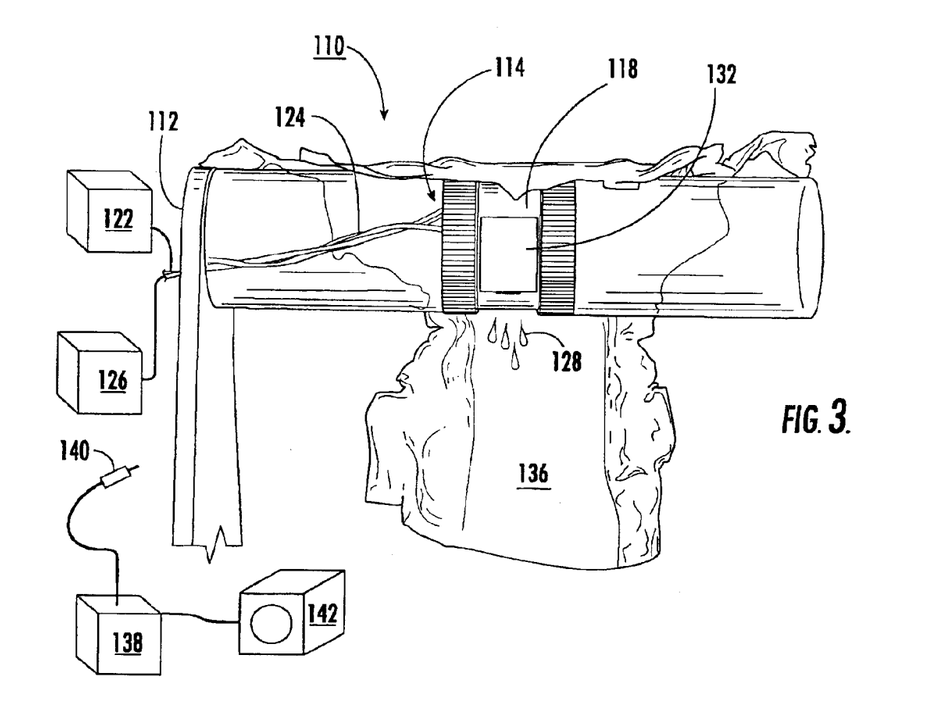
FIG. 3 is a perspective view of the simulated skin attached to a heated mechanical arm in accordance with another aspect of the invention.

FIG. 3 shows another embodiment of the invention in which an evaluation apparatus 110 includes an arm 112 with an attachment area 114 and an injection port (not shown) through which a fluid tube 124 is inserted. A heater 118 is disposed about the attachment area 114 and a simulated skin 132 is attached to the heater 118. In this aspect, the heater 118 has a heater hole (not shown) through which the fluid tube 124 is also at least partially inserted. It is to be noted that the heater 118 can be a removable heater cuff, a removable heater pad, an embedded heater element, and similar heater components that can be powered by an electricity source 122. It is to be further noted, as in the previous embodiment, that the fluid tube 124 can be arranged internally or externally relative to the apparatus 110 and/or the heater 118 without affecting fluid loading operations.

Also shown in FIG. 3 are a fluid delivery device 126, a measuring device 138 with probe 140, and a monitor 142. These elements are similar to those of the previous embodiment, i.e., the fluid delivery device 26, measuring device 38 with probe 40, and monitor 42 respectively detailed above.

Also similar to the foregoing embodiment, a variety of simulated skin materials and products are suitable for use as the simulated skin 132 to demonstrate the hydration and/or moisturization properties of personal care products, diapers and the like. Examples of simulated skin 132 include but are not limited to VITRO-SKIN™ and VITRO-CORNEUM® available from IMS Inc., Milford, Conn., TEST SKIN™ II from Organogenesis Inc., Canton, Mass., SKINETHIC® from Skinethic Tissue Culture Laboratories, Nice, France, collagen in a sausage casing, chamois, and similar materials as described previously.

By way of example operation, the material 136 (seen partially detached for clarity in FIG. 3) is securely wrapped about the arm 112 to at least partially cover the heater 118 and the skin 132. The fluid delivery device 126 delivers a fluid 128 into the material 136. The fluid 128 can be water, saline, a solution of 0.9% sodium chloride, a colored solution, an exudate or any suitable liquid or other material for simulating human body fluids. After a predetermined time, e.g., 30–90 minutes, the material 136 is removed followed by removal of the simulated skin 132. The simulated skin 132 is quickly placed on a deformable surface such as a cosmetic sponge, conventional sponge, or the like to simulate a subcutaneous layer of skin.

It is to be noted that the sponge in one aspect could be mounted or affixed substantially flatly to the arm 112 with the skin 132 disposed on the sponge. Therefore, the TEWL measurements can be conducted directly on the skin 132 while it is on the sponge. After a predetermined time, the arm 112 can be swiveled about a base as described in the foregoing embodiment to evaluate the skin 132. However, the sponge is not required to make direct measurements on the arm 112 since the skin 132 can be removed and measured remotely from the arm 112 as described above.

Operation of the apparatus 110 is further described in the following protocols and experiments, are taken by the measuring device 138 and its probe 140 as previously described.

I. Experiment Conducted on an Exemplary Embodiment of the Invention

Results derived from experiments conducted in accordance with one exemplary embodiment of the present invention are as follows. In the following pooling experiment, a diaper was tested on the evaluation apparatus 10 illustrated in FIG. 1. As used herein, pooling is defined as occurring when a surface is wet In this example, pooling occurs when the skin 32 becomes wet. It is undesirable to have that portion of an absorbent article that contacts a user to become wet since the complementary portion of the user's skin contacting the wet absorbent article will also be wet. This is undesirable both hygienically and because it is uncomfortable to the user.

In this experiment, a Step 3 Ultra-Trim® diaper was used as the material or diaper 36. The diaper 36 was attached about the heater 18 proximate the attachment area 14. The digital pump 26, capable of less than 1 cubic centimeter to over 800 cubic centimeters was set to insult 60 cc/min of simulated physiological fluid or warmed saline 28 in 12 seconds. The digital pump 26 was further programmed to insult the diaper 36 with saline 28 three times. The diaper 36 was marked with a target measurement zone (not shown)

15.2 cm from a top front of the diaper 36 on its inside. The back of the diaper 36 was marked on its outside approximately 5 cm from the top. The target-loading zone should be measured and marked 21.2 cm from the top of the diaper 36. The target loading zone was lined up directly under the tube 24 on the under side of the arm 12 with the front of the diaper 36 at the top. The back of the diaper 36 was wrapped around the arm 12 and securely taped with the back of the diaper located on the top of the arm 12 and folded to the inside at the 5 cm mark. The diaper 36 is insulted with the saline 28 three times and evaluated after 30–90 minutes.

Result: Upon first injection of the saline 28 into the diaper 36, the evaluation apparatus 10 was successful in this pooling evaluation.

II. Experiment Conducted on another Exemplary Embodiment of the Invention

Exemplary Procedure

Results derived from experiments conducted in accordance with another exemplary embodiment of the present invention are as follows. In this experiment with particular reference to FIGS. 1 and 4, the following test procedure employed a diaper 36 tested on the mechanical arm 12:

1. Preheat the mechanical arm (12) to 95° F. before beginning.
2. Turn on the computer (38) and DermaLabe instrument (40). Warm up according to manufacturer's directions.
3. Turn on the fluid delivery device (26).
4. Calibrate the fluid delivery device (26) prior to use.
5. Measure and mark TEWL measurement zone 15.2 cm from the top inside edge of a Step 3 diaper (36).
6. Measure and mark Loading Zone—21.2 cm from the top inside edge of a Step 3 diaper (36).
7. Using an unused piece or patch (32) of simulated skin—for this experiment, a 5 cm×3.8 cm patch of VITRO-SKI™ was used—place it securely on the side of the mechanical arm (12) using waterproof surgical tape. The VITRO-SKIN™ should be on the side facing the experimenter (rough side out), approximately 0.75 cm from the top of the heating element (not shown).
8. Place the diaper (36) on the arm (12) with the front waistband facing the experimenter. Align the TEWL measurement zone (15.2 cm) on the diaper (36) with the patch (32). The diaper (36) should be wrapped down and around the arm (12) with the back of the diaper (36) slightly folded. The front waistband wraps slightly over the back. Ensure that the loading tube (24) embedded in the arm (12) lines up with the loading zone on the diaper (36). The diaper (36) is secured on the arm (12) by masking tape. The tape is tightly wrapped around both ends of the diaper (36).
9. Use program 3S300T45 on the computer in the WIN-LIN software. Press start to begin the loading procedure. 60 milliliter/second (mls) of saline (28) should begin to flow into the diaper (36) at 300 cc/mm every 45 seconds, three times or a total load of 180 mls.
10. After the third and final insult, set and start a timer for 60 minutes.
11. After 60 minutes, open the diaper (36) and quickly remove the patch (32) from the arm (12) and place the patch (32) on a cosmetic sponge (not shown) for a TEWL measurement.
12. Record the TEWL measurement in a notebook, and save same to a Microsoft® Excel file.

Exemplary Results

The initial TEWL value for the patch (32) prior to use on the arm (12) was zero g/m$^2$/hr. The patch (32) was conditioned in a controlled laboratory setting at 72° Fahrenheit +/-2° Fahrenheit, 40% RH +/-5%. Typically, a baseline TEWL measurement is taken on human skin prior to conducting known Clinical Research Service (CRS) Adult Armband Testing. The baseline value is then subtracted from the final TEWL value for a trans-epidermal water loss measurement in units of g/m$^2$/hr. For this experiment, since the initial TEWL value was zero g/m$^2$/hr, no subtraction was necessary.

A strong correlation was shown between the CRS Armband Test versus this exemplary experiment ($R^2$=0.958). This indicates that using a mechanical apparatus as a screening tool for materials and components of products is effective and practical.

Moreover, in a small-scale study two groups of diapers 36, each numbering ten diapers, were evaluated three weeks apart using the foregoing protocol with no significant differences detected between the two groups of diapers 36 from the same bag and lot number. The study therefore shows that the testing is repeatable with at least a 95% confidence level.

Based on the strong correlation between the CRS Armband Test and this mechanical experiment and its repeatability, the experiment can be used as a bench test for test equipment and pre-screening materials for skin dryness for use in final product testing. However, it is to be understood that the experiment may also be used to screen competitive products, perform other research and development and the like and is not limited to the foregoing exemplary uses.

A method for evaluating a material with a fluid from fluid delivery device is provided in another aspect of the invention. The method includes providing an evaluation apparatus 10 with an object 12 as previously introduced. A heater 18 with a heater hole 20 is wrapped about an attachment area 14 of the object 12 and at least partially covers the object 12. The heater 18 is at least partially covered with an artificial skin 32 and the skin 32 is at least partially covered with an evaluation material 36. Further steps include interposing fluid 28 such as saline from the fluid delivery device 26 between the heater 18 and the material 36 via the heater hole 20. In one aspect, the fluid 28 is warmed and insulted into or near the material 36 at between 50 cubic centimeters/minute (cc/min) to about 65 cc/min of the warmed fluid 28 for about 10 to about 15 seconds. It should be noted that these volumes and lengths of time are by way of example only and may be varied to simulate sweat glands and other orifices of babies, children and adults. The steps of this method may further include assessing the fluid insulted material 36 and a condition of the artificial skin 32 to determine suitability of the material 36 for further screening and/or dryness and wetness of the skin 32. Additionally, the heater 18 may be heated from between 70 to about 120 degrees Fahrenheit to further simulate human skin temperature (e.g. from about 92 degrees Fahrenheit to about 99 degrees Fahrenheit) prior to insulting the material 36 with fluid 28.

Experiment on an Exemplary Embodiment of the Present Invention

Results derived from experiments conducted in accordance with one exemplary embodiment of the present invention are as follows. In this experiment with particular reference to FIG. 1, the following test procedure employed a diaper 36 tested on the mannequin torso 12:

Exemplary Procedure

1. Preheat the mannequin (12) to 94° Fahrenheit and saline (28) to 35° C. (95° F.).
2. Turn on the computer (38) and DermaLab® instrument (40). Warm up according to manufacturer's directions.
3. Loading Zone—measure and mark 21.2 cm from the top inside edge of a Step 3 diaper (36).
4. Take the mannequin (12) off the stand (not shown) and lay on its back.
5. Check position of the saline tube (24). Ensure it has not moved and is located inside at the center rear opening of the mannequin (12).
6. Position the diaper (36) under the mannequin (12).
7. Using an unused piece or patch (32) of simulated skin—for this experiment, a 2"×1.5" patch of VITRO-SKIN™ was used—position the patch (32) on the front of the mannequin (12). The patch (32) will be centered on the mark (not shown) on the mannequin (12), approximately 8.57 cm from the center of the saline loading tube (24) to the center of the patch (32). The rough side of the patch (32) must be up. Tape is not needed.
8. Place the diaper on the mannequin (12) with the front waistband facing the experimenter. Align the TEWL measurement zone (15.2 cm) on the diaper (36) with the patch (32). Ensure that the loading tube (24) embedded in the mannequin (12) lines up with the loading zone on the diaper (36).
9. Close the diaper (36).
10. Replace the mannequin (12) on its stand.
11. Insult the diaper (36) with the saline (28) three times, 60 milliliters per second (mls) each time, with a fluid deliver device (not shown). The saline (28) is warmed to 35° C. prior to insulting the diaper (36). The insults should be 45 seconds apart.
12. After the third and final insult, set and start a timer for 60 minutes.
13. After 60 minutes, open the diaper (36) and quickly remove the patch (32) from the mannequin (12) and place it on a cosmetic sponge (not shown) for a TEWL measurement.
14. Take a TEWL measurement on the center of the patch (32).
15. Record the TEWL output in a notebook, and save same to a Microsoft® Excel file.

Exemplary Results

The initial TEWL value for the patch (32) prior to use on the mannequin (12) was zero $g/m^2/hr$. The patch (32) was conditioned in a controlled laboratory setting at 72° Fahrenheit +/−2° Fahrenheit, 40% RH +/−5%. Typically, a baseline TEWL measurement is taken on human skin prior to conducting known Clinical Research Service (CRS) Adult Armband Testing. The baseline value is then subtracted from the final TEWL value for a trans-epidermal water loss measurement in units of $g/m^2/hr$. For this experiment, since the initial TEWL value was zero $g/m^2/hr$, no subtraction was necessary.

A strong correlation was shown between the CRS Armband Test versus this exemplary experiment ($R^2$ 0.958). This indicates that using a mechanical apparatus as a screening tool for materials and components of products is practical.

Moreover, in a small-scale study two groups of diapers 36, each numbering ten diapers, were evaluated three weeks apart using the foregoing protocol with no significant differences detected between the two groups of diapers 36 from the same bag and lot number. The study therefore shows that the testing is repeatable with at least a 95% confidence level.

Based on the strong correlation between the CRS Armband Test and the mechanical experiment and its repeatability, the experiment can be used as a bench test for test equipment and pre-screening materials for skin dryness for use in final product testing. However, it is to be understood that the experiment may also be used to screen competitive products, perform other research and development, and the like and is not limited to the foregoing exemplary uses.

III. Experiment Conducted on a further Exemplary Embodiment of the Present Invention

Exemplary Procedure

Results derived from experiments conducted in accordance with another exemplary embodiment of the present invention are as follows. In this experiment with particular reference to FIG. 4, the following test procedure employed a diaper 36 tested on the mechanical arm 12:

1. An acrylic tube or "arm" 12 having an outer diameter of 3.25 inches (8.25 cm) was mounted onto a stand 30 parallel to the ground.
2. A piece of VITRO-SKIN™ (6.5 cm by 6.5 cm) of formulation 5X-2G-19 is used as skin 32. The skin 32 is weighed and taped to the arm 12 using scotch tape.
3. A Step 3 size Huggies® Ultratrim diaper 36 is wrapped around the arm 12 as would be done in an armband TEWL study, with the target on the bottom side of the arm 12 at the point of fluid introduction.
4. The diaper 36 is secured around the arm with masking tape.
5. Three insults of 60 ml of saline are introduced into the diaper 36, between the skin 32 and the diaper 36, at a rate of 5 cc/sec at 45 second intervals.
6. The diaper 36 remains on the arm 12 for 1 hour after the final insult.
7. After the diaper 36 is removed, the skin 32 is weighed again.
8. A difference in weights is calculated and normalized to the area of the skin 32.
9. Results are reported in $g/m^2/hr$ and are referred to as pick-up values.

Products that have been tested in armband TEWL were also tested with this test method. The present test has been used to distinguish between the poor and the good performing products. For example, a knit polyester liner of 220 denier fibers that has been thermoformed with ¼ inch bumps consistently performs better than a standard diaper liner in an armband TEWL with up to a 40% TEWL reduction.

The knit polyester liner also performed better than standard diaper liner with this experimental test method. Specifically, a 38% decrease in pick-up from the control was measured with the knit liner. The control product, or standard Huggies® Ultratrim diaper liner, had a pick-up of 91 $g/m^2/hr$ with a standard deviation of 14. The knit polyester liner had a measured pick-up of 56 $g/m^2/hr$ with a standard deviation of 5. Both products were tested with a sample size of 3. The percentage decrease measured with the experimental test method does not match the decrease in armband TEWL, but shows a directional relationship.

It is to be understood that the above exemplary values are not intended as limitations of the invention. For instance, the substrate can be sized from about 2 $cm^2$ to about 100 $cm^2$. Additionally, the fluid can be insulted in the material from about 45 ml to about 250 ml at a rate of about 1 cc/sec to about 15 cc/sec and at about 30 second intervals to about 60 minute intervals. Furthermore, the fluid-insulted material can be left on the artificial arm for about 30 minutes to about 5 hours, more particularly about 1 hour after a final insult.

The foregoing test method illustrates that materials and products can be ranked using an artificial arm and simulated skin substrate with similar results to armband TEWL rankings. In other words, this method can be used to prescreen any materials and systems that are presently tested with TEWL. It is also to be noted that this method is applicable to infant, child, and adult care products.

While preferred embodiments of the invention have been shown and described, those skilled in the art will recognize that other changes and modifications may be made to the foregoing embodiments without departing from the spirit and scope of the invention. For example, specific shapes of various elements of the illustrated embodiment may be altered to suit particular applications such as shaping the object 12 as a lower torso mannequin, an upper torso mannequin, a full body mannequin, a mannequin forearm, a mannequin hand, a mannequin leg, a mannequin foot, a mannequin head and various other portions of a human body. It is intended to claim all such changes and modifications as fall within the scope of the appended claims and their equivalents.

That which is claimed is:

1. A method for evaluating a material using a substrate, the method comprising the steps of:
    attaching the substrate to an object;
    at least partially covering the substrate with a material;
    insulting the material with a fluid;
    removing the fluid-insulted material prior to assessing the condition of the substrate; and
    assessing a dryness or wetness of the fluid-insulted material from a condition of the substrate using a measuring device configured to measure the condition of the substrate by one of capacitance, conductance, electrical impedance, or transepidermal water loss.

2. The method as in claim 1, wherein the substrate is selected from the group consisting of a medical grade collagen film, a collagen disposed in a sausage casing, a chamois, a cellulose film, a cultured skin substrate, a bioengineered skin, a living skin sample, a dead skin sample and combinations thereof.

3. The method as in claim 1 further comprising the step of heating the substrate with a heater from between 70° F. to about 120° F. to simulate human skin temperature, the heater disposed on the object proximate the substrate.

4. The method as in claim 3, wherein the heater defines a hole therethrough, the hole configured for passage of the fluid into the material.

5. The method of claim 4, wherein the substrate is disposed from between 5 cm to about 9 cm from the hole.

6. The method as in claim 4, wherein the substrate defines an opening therein, the substrate opening and the hole cooperable to simulate an aperture selected from the group consisting of a tear duct, a urethra, a pore, a vaginal opening, a body cavity, and combinations thereof.

7. The method as in claim 4, further comprising a tubing, the fluid delivery device and the tubing cooperably configured to deliver the fluid through the hole to insult the material.

8. The method as in claim 1, further comprising a fluid delivery device, the fluid delivery device configured to deliver a measured quantity of the fluid to insult the material.

9. The method as in claim 1, wherein the object is selected from the group consisting of a lower-torso mannequin, an upper-torso mannequin, a full-body mannequin, a mannequin forearm, a mannequin hand, a mannequin leg, a mannequin foot, a mannequin head, and combinations thereof.

10. The method as in claim 1, wherein the object is formed of a substance selected from the group consisting of a silicone, a neoprene, a plastic, an acetyl plastic, an acrylic plastic, an elastomeric material, a high density polyethylene, a polymer, a metal, a glass, a composite material and combinations thereof.

11. The method as in claim 1, wherein the material is a absorbent article selected from the group consisting of disposable or non-disposable diapers, disposable or non-disposable adult incontinence products, disposable or non-disposable feminine products, nursing healthcare products, disposable or non-disposable child training pants, face masks, bandages, gloves and combinations thereof.

12. The method as in claim 1, wherein the fluid is selected from the group consisting of water, saline, synthetic or natural menses, synthetic or natural urine, artificial or natural breast milk, synthetic or natural blood, 0.9% sodium chloride solution, colored solution, an exudate, and combinations thereof.

13. The method as in claim 1, further comprising the steps of removing the substrate from the object and placing the substrate on a layer to assess the condition of the substrate, the layer configured to simulate a subcutaneous skin.

14. The method as in claim 13, wherein the layer is selected from the group consisting of a sponge, a cosmetic sponge, a rubber article, and combinations thereof.

15. A method for evaluating a material insulted with a fluid, the method comprising the steps of:
    providing an object having a fluid injection port therethrough and a heater arrangement having a hole therethrough, the fluid injection port and the heater hole cooperable to simulate a human orifice;
    at least partially covering the object with a substrate, the substrate disposed proximate the heater arrangement;
    at least partially covering the substrate with a material;
    insulting a fluid from a fluid delivery device into the material via the fluid injection port and the hole;
    leaving the material at least partially covering the substrate for a predetermined period before removing the material to assess the condition of the simulated skin; and
    assessing the fluid-insulted material and a condition of the substrate by one of capacitance, conductance, electrical impedance, or transepidermal water loss.

16. The method as in claim 15, wherein the object is selected from the group consisting of a lower-torso mannequin, an upper-torso mannequin, a full-body mannequin, a mannequin forearm, a mannequin hand, a mannequin leg, a mannequin foot, a mannequin head, and combinations thereof.

17. The method as in claim 15, wherein the object is formed of a base material selected from the group consisting of a silicone, a neoprene, a plastic, an acetyl plastic, an acrylic plastic, an elastomeric material, a high density polyethylene, a polymer, a metal, a glass, a composite material and combinations thereof.

18. The method as in claim 15, wherein the substrate is selected from the group consisting of a medical grade collagen film, a collagen disposed in a sausage casing, a chamois, a cellulose film, a cultured skin substrate, a bioengineered skin, a living skin sample, a dead skin sample and combinations thereof.

19. The method as in claim 15, wherein the substrate is disposed apart from the hole from between 5 cm to about 10 cm.

20. The method as in claim 15, further comprising the step of heating the substrate with the heater arrangement from between 70° F. to about 120° F. to simulate human skin temperature.

21. The method as in claim 20, wherein the heater arrangement is selected from the group consisting of a removable heater cuff, a removable heater pad, an embedded heater element, and combinations thereof.

22. The method as in claim 15, further comprising a tubing, the fluid delivery device and the tubing cooperably configured to insult the fluid through the hole.

23. The method as in claim 15, wherein the material is a absorbent article selected from the group consisting of disposable or non-disposable diapers, disposable or non-disposable adult incontinence products, disposable or non-disposable feminine products, nursing healthcare products, disposable or non-disposable child training pants, face masks, bandages, gloves and combinations thereof.

24. The method as in claim 15, further comprising the step of warming the fluid to a normal human temperature prior to insulting the material.

25. The method for evaluating a material as in claim 24, further comprising the step of insulting the material with between about 50 cc/min to about 65 cc/min of the warmed fluid within about 10 seconds to about 15 seconds.

26. The method as in claim 24, further comprising the substep of insulting 300 cc/min of the warmed fluid approximately every 45 seconds.

27. The method as in claim 15, wherein the predetermined period is from between 30 minutes to about 90 minutes.

28. The method as in claim 15, further comprising the steps of displaying the assessed condition of the substrate on a monitor and recording the assessed condition.

* * * * *

UNITED STATES PATENT AND TRADEMARK OFFICE
CERTIFICATE OF CORRECTION

PATENT NO. : 6,904,820 B2 Page 1 of 1
APPLICATION NO. : 10/324605
DATED : June 14, 2005
INVENTOR(S) : Tate et al.

It is certified that error appears in the above-identified patent and that said Letters Patent is hereby corrected as shown below:

on the title page item (75), delete --Jason Cohen-- and insert "Jason C. Cohen".

Column 11, line 46 delete --70° F.-- and insert "70° F"

Column 11, line 47 delete --120° F.-- and insert "120° F"

Column 13, line 3 delete --70° F. to about 120° F.-- and insert "70° F to about 120° F"

Signed and Sealed this

Twenty-ninth Day of August, 2006

JON W. DUDAS
*Director of the United States Patent and Trademark Office*